United States Patent
Savage et al.

(10) Patent No.: US 9,320,597 B2
(45) Date of Patent: *Apr. 26, 2016

(54) TRANSCATHETER PROSTHETIC HEART VALVE DELIVERY SYSTEM WITH RECAPTURING FEATURE AND METHOD

(75) Inventors: Padraig J. Savage, Dromcollogher (IE); Gianfranco M. Pellegrini, Santa Rosa, CA (US); Finn O. Rinne, Santa Rosa, CA (US); Matthew J. Rust, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 496 days.

This patent is subject to a terminal disclaimer.

(21) Appl. No.: 12/750,490

(22) Filed: Mar. 30, 2010

(65) Prior Publication Data
US 2011/0245917 A1 Oct. 6, 2011

(51) Int. Cl.
*A61F 2/24* (2006.01)
*A61F 2/95* (2013.01)

(52) U.S. Cl.
CPC ............. *A61F 2/2427* (2013.01); *A61F 2/2436* (2013.01); *A61F 2002/9534* (2013.01)

(58) Field of Classification Search
CPC .............. A61F 2002/9517; A61F 2/95; A61F 2002/9534; A61F 2/2436
USPC ................................ 623/2.1, 2.11, 2.12, 1.11
See application file for complete search history.

(56) References Cited

U.S. PATENT DOCUMENTS

| | | | |
|---|---|---|---|
| 6,203,550 | B1 | 3/2001 | Olson |
| 2002/0002396 | A1* | 1/2002 | Fulkerson .................... 623/1.11 |
| 2003/0236545 | A1 | 12/2003 | Gilson |
| 2006/0265056 | A1* | 11/2006 | Nguyen et al. ............... 623/2.18 |
| 2007/0088431 | A1 | 4/2007 | Bourang et al. |
| 2007/0239254 | A1 | 10/2007 | Chia et al. |
| 2007/0270932 | A1 | 11/2007 | Headley et al. |
| 2008/0234797 | A1 | 9/2008 | Styrc |
| 2008/0255651 | A1 | 10/2008 | Dwork |
| 2008/0262592 | A1 | 10/2008 | Jordan et al. |
| 2009/0093876 | A1 | 4/2009 | Nitzan et al. |

FOREIGN PATENT DOCUMENTS

| | | |
|---|---|---|
| WO | WO2008/028569 | 3/2008 |
| WO | WO2008/125153 | 10/2008 |
| WO | WO2009/092782 | 7/2009 |

* cited by examiner

*Primary Examiner* — Katherine M Shi (57) ABSTRACT

A delivery system for percutaneously deploying a stented prosthetic heart valve. The system includes a delivery capsule and a recapture assembly. The capsule is configured to compressively retain the prosthesis. The recapture assembly includes a frame and sleeve attached to the frame. The recapture assembly is transitionable from a compressed arrangement to an expanded arrangement with a distally increasing diameter.

15 Claims, 4 Drawing Sheets

TRANSCATHETER PROSTHETIC HEART VALVE DELIVERY SYSTEM WITH RECAPTURING FEATURE AND METHOD

BACKGROUND

The present disclosure relates to systems and methods for percutaneous implantation of a heart valve prosthesis. More particularly, it relates to systems and methods for transcatheter implantation of a stented prosthetic heart valve, including partial deployment, recapturing, and repositioning of the prosthesis at the implantation site.

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With these percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be repaired (e.g., the aortic valve annulus). Although transcatheter techniques have attained widespread acceptance with respect to the delivery of conventional stents to restore vessel patency, only mixed results have been realized with percutaneous delivery of a relatively more complex prosthetic heart valve.

Various types and configurations of prosthetic heart valves are available for percutaneous valve procedures, and continue to be refined. The actual shape and configuration of any particular prosthetic heart valve is dependent to some extent upon the native shape and size of the valve being repaired (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation systems, the stent frame of the valved stent is made of a self-expanding material and construction. With these systems, the valved stent is crimped down to a desired size and held in that compressed arrangement within an outer sheath, for example. Retracting the sheath from the valved stent allows the stent to self-expand to a larger diameter, such as when the valved stent is in a desired position within a patient. In other percutaneous implantation systems, the valved stent can be initially provided in an expanded or uncrimped condition, then crimped or compressed on a balloon portion of catheter until it is as close to the diameter of the catheter as possible. Once delivered to the implantation site, the balloon in inflated to deploy the prosthesis. With either of these types of percutaneous stent delivery systems, conventional sewing of the prosthetic heart valve to the patient's native tissue is typically not necessary.

It is imperative that the stented prosthetic heart valve be accurately located relative to the native annulus immediately prior to full deployment from the catheter as successful implantation requires the prosthetic heart valve intimately lodge and seal against the native annulus. If the prosthesis is incorrectly positioned relative to the native annulus, serious complications can result as the deployed device can leak and may even dislodge from the native valve implantation site. As a point of reference, this same concern does not arise in the context of other vascular stents; with these procedures, if the target site is "missed," another stent is simply deployed to "make-up" the difference.

While imaging technology can be employed as part of the implantation procedure to assist a clinician in better evaluating a location of the transcatheter prosthetic heart valve immediately prior to deployment, in many instances, this evaluation alone is insufficient. Instead, clinicians desire the ability to partially deploy the prosthesis, evaluate a position relative to the native annulus, and reposition the prosthesis prior to full deployment if deemed necessary. Repositioning, in some instances, can require the prosthesis first be re-compressed and re-located back within the outer delivery sheath. Stated otherwise, the partially deployed stented prosthetic heart valve can be "recaptured" by the delivery system, and in particular within the outer sheath. While, in theory, the recapturing of a partially deployed stented prosthetic heart valve is straight forward, in actual practice, the constraints presented by the implantation site and the stented heart valve itself render the technique exceedingly difficult.

For example, the stented heart valve is purposefully designed to rigidly resist collapsing forces once deployed to properly anchor itself in the anatomy of the heart. Thus, whatever tooling is employed to force a partially-deployed segment of the prosthesis back to a collapsed arrangement must be capable of exerting a significant radial force. Conversely, however, the tooling cannot be overly rigid to avoid damaging the transcatheter heart valve as part of a recapturing procedure. Along these same lines, the aortic arch must be traversed, necessitating that the delivery system provide sufficient articulation attributes. Unfortunately, existing delivery systems do not consider, let alone optimally address, these and other issues.

Figure 1A:
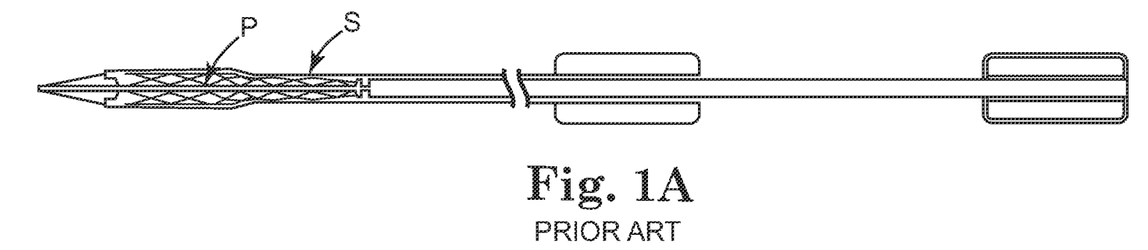
FIGS. 1A-1C are simplified side views illustrating deficiencies of existing stent delivery sheaths or catheters to effectuate recapture of a partially deployed stented prosthetic heart valve.
Figure 1B:
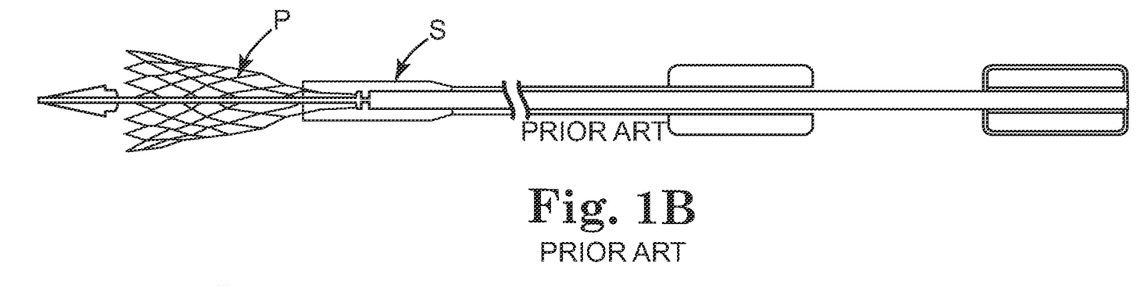
Figure 1C:
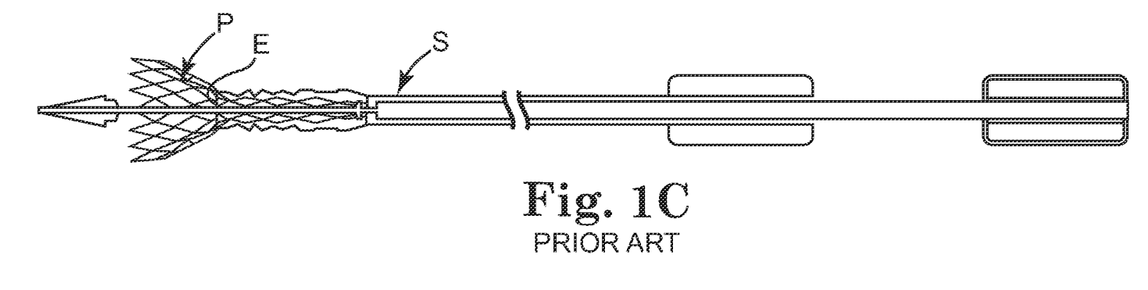

As mentioned above, an outer sheath or catheter is conventionally employed to deliver a self-deploying vascular stent. Applying this same technique for the delivery of a self-deploying stented prosthetic heart valve, the high radial expansion force associated with the prosthesis is not problematic for complete deployment as the outer sheath is simply retracted in tension to allow the prosthetic heart valve to deploy. Were the conventional delivery system operated to only partially withdraw the outer sheath relative to the prosthesis, only the so-exposed distal region of the prosthetic would expand while the proximal region remains coupled to the delivery system. In theory, the outer sheath could simply be advanced distally to recapture the expanded region. Unfortunately, with conventional sheath configurations, attempting to compress the expanded region of the stented prosthetic heart valve by distally sliding the sheath is unlikely to be successful. The conventional delivery sheath cannot readily overcome the radial force of the expanded region of the prosthesis because, in effect, the sheath is placed into compression and will collapse due at least in part to the abrupt edge of the sheath being unable to cleanly slide over the expanded region of the prosthesis. This effect is illustrated in a simplified form in FIGS. 1A-1C. Prior to deployment (FIG. 1A), the stented prosthetic heart valve P is constrained within, and supports, the sheath S. With deployment (FIG. 1B), the sheath S is distally retracted, and the prosthesis P partially deploys.

Where an attempt made to "recapture" the prosthesis P by distally sliding the sheath (FIG. 1C), a leading end E of the sheath S abruptly abuts against the enlarged diameter of the prosthesis P, such that the distal end E cannot readily slide over the prosthesis P. Further, the sheath S is no longer internally supported and the radially expanded bias of the prosthesis P causes the sheath S to buckle or collapse.

In light of the above, a need exists for a stented transcatheter prosthetic heart valve delivery system and method that satisfies the constraints associated with heart valve implantation and permits partial deployment and recapturing of the prosthesis.

SUMMARY

Some aspects in accordance with principles of the present disclosure relate to a delivery system for percutaneously deploying a stented prosthetic heart valve. The prosthetic heart valve is radially self-expandable from a compressed arrangement to a natural arrangement. The delivery system includes an inner shaft assembly, a delivery sheath capsule, and a recapture assembly. The inner shaft assembly includes an intermediate region providing a coupling structure configured to selectively engage a stented prosthetic heart valve. The delivery sheath capsule is slidably disposed over the inner shaft assembly and is configured to compressively retain a stented prosthetic heart valve engaged with the coupling structure. The recapture assembly is slidably disposed over the inner shaft assembly and includes a recapture frame and sleeve coupled to the frame. The frame is transitionable from a compressed arrangement to an expanded arrangement in which the frame forms a funnel shape having a distally increasing diameter as the delivery sheath capsule is retracted. With this construction, the delivery system is configured to provide a loaded state in which the capsule compressively retains the stented prosthetic heart valve over the inner shaft assembly and the recapture assembly is longitudinally displaced from the prosthetic heart valve. During use, the recapture assembly can be employed to facilitate sliding of the recapture frame over a partially deployed region of the prosthetic heart valve as part of a recapturing operation. The recapture frame is configured to provide a columnar strength to the recapture assembly, with the sleeve providing a surface to engage and slide over a partially deployed prosthetic heart valve.

Yet other aspects in accordance with principles of the present disclosure relate to a device for repairing a heart valve of a patient. The device includes a delivery system and a prosthetic heart valve. The delivery system includes the inner shaft assembly, the delivery sheath capsule, and the recapture assembly, including the recapture frame and sleeve, as described above. The prosthetic heart valve has a stent frame and a valve structure forming at least two valve leaflets attached to the stent frame. With this construction, the prosthetic heart valve is self-expandable from a compressed arrangement to a natural arrangement. With this construction, the device is configured to be transitionable between a loaded state, a partially deployed state, and a recapturing state. In the loaded state, the prosthetic heart valve is coupled to the intermediate region of the inner shaft assembly, with the capsule compressively retaining the prosthetic heart valve in the compressed arrangement. Further, the recapture assembly is longitudinally spaced from the prosthetic heart valve. In the partially deployed state, the capsule is at least partially withdrawn from the prosthetic heart valve such that a distal region of the prosthetic heart valve is exposed relative to the capsule and self-expands. In the recapturing state, the recapture assembly is positioned distal the capsule and along the distal exposed region of the prosthetic heart valve, causing the recapture frame to expand toward the expanded condition to recapture the prosthetic heart valve.

Yet other aspects in accordance with principles of the present disclosure relate to a method of deploying a stented prosthetic heart valve to an implantation site. The method includes receiving a delivery system loaded with a radially expandable prosthetic heart valve having a stent frame to which a valve structure is attached. The delivery system includes a delivery sheath capsule compressively containing the prosthetic heart valve in a compressed arrangement over an inner shaft assembly in a loaded state, as well as a recapture assembly including a frame and sleeve slidably disposed over the inner shaft assembly. In the loaded state, the recapture assembly is longitudinally spaced from the prosthetic heart valve. The prosthetic heart valve is delivered, in the compressed arrangement, through a bodily lumen of the patient and to the implantation site via the delivery system in the loaded state. The capsule is proximally retracted relative to the prosthetic heart valve such that a distal region of the prosthetic heart valve is exposed distal the capsule. The exposed, distal region self-expands toward a deployed arrangement. A position of the partially deployed prosthetic heart valve relative to the implantation site is evaluated. Based upon the evaluation, the recapture assembly is distally advanced relative to the prosthetic heart valve such that the recapture assembly is distally advanced over the prosthetic heart valve.

DETAILED DESCRIPTION

Current transcatheter heart valve delivery systems do not have the capability of transcatheter valve repositioning in the antegrade or retrograde directions after deployment. The delivery systems of the present disclosure overcome these problems, and permit the clinician to partially deploy the prosthetic heart valve, and prior to release, reposition or recapture and remove it. In general terms, the system functions by providing a recapture assembly having a recapture frame and sleeve that serves as a transition between the delivery sheath capsule and an expanded region of a partially deployed prosthesis to effectuate recapturing of the partially deployed prosthetic heart valve.

As referred to herein, the prosthetic heart valve as used in accordance with the various systems, devices, and methods of the present disclosure may include a wide variety of different configurations, such as a bioprosthetic heart valve having tissue leaflets or a synthetic heart valve having a polymeric, metallic, or tissue-engineered leaflets, and can be specifically configured for replacing any heart valve. Thus, the prosthetic heart valve useful with the systems, devices, and methods of the present disclosure can be generally used for replacement of a native aortic, mitral, pulmonic, or tricuspid valves, for use as a venous valve, or to replace a failed bioprosthesis, such as in the area of an aortic valve or mitral valve, for example.

In general terms, the prosthetic heart valves of the present disclosure include a stent or stent frame maintaining a valve structure (tissue or synthetic), with the stent having a normal, expanded arrangement and collapsible to a compressed arrangement for loading within the delivery system. The stent is normally constructed to self-deploy or self-expand when released from the delivery system. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a verity of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine, porcine or equine paracardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaftlets; however, replacement prosthetic heart valves of the types described herein can incorporate more or less than three leaflets.

Some embodiments of the stent frames can be a series of wires or wire segments arranged such that they are capable of self-transitioning from a collapsed arrangement to a normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the natural, expanded arrangement. In the collapsed arrangement, such a stent frame support structure with attached valves can be mounted onto a delivery system. The stent frame support structures are configured so that they can be changed to their natural, expanded arrangement when desired, such as by the relative movement of one or more sheaths relative to a length of the stent frame.

The wires of these stent frame support structures in embodiments of the present disclosure can be formed from a shape memory material such as a nickel titanium alloy (e.g., Nitinol™). With this material, the support structure is self-expandable from the compressed arrangement to the natural, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery system that can be used includes a catheter with a retractable sheath that covers the stent frame until it is to be deployed, at which point the sheath can be retracted to allow the stent frame to self-expand. Further details of such embodiments are discussed below.

Figure 2:
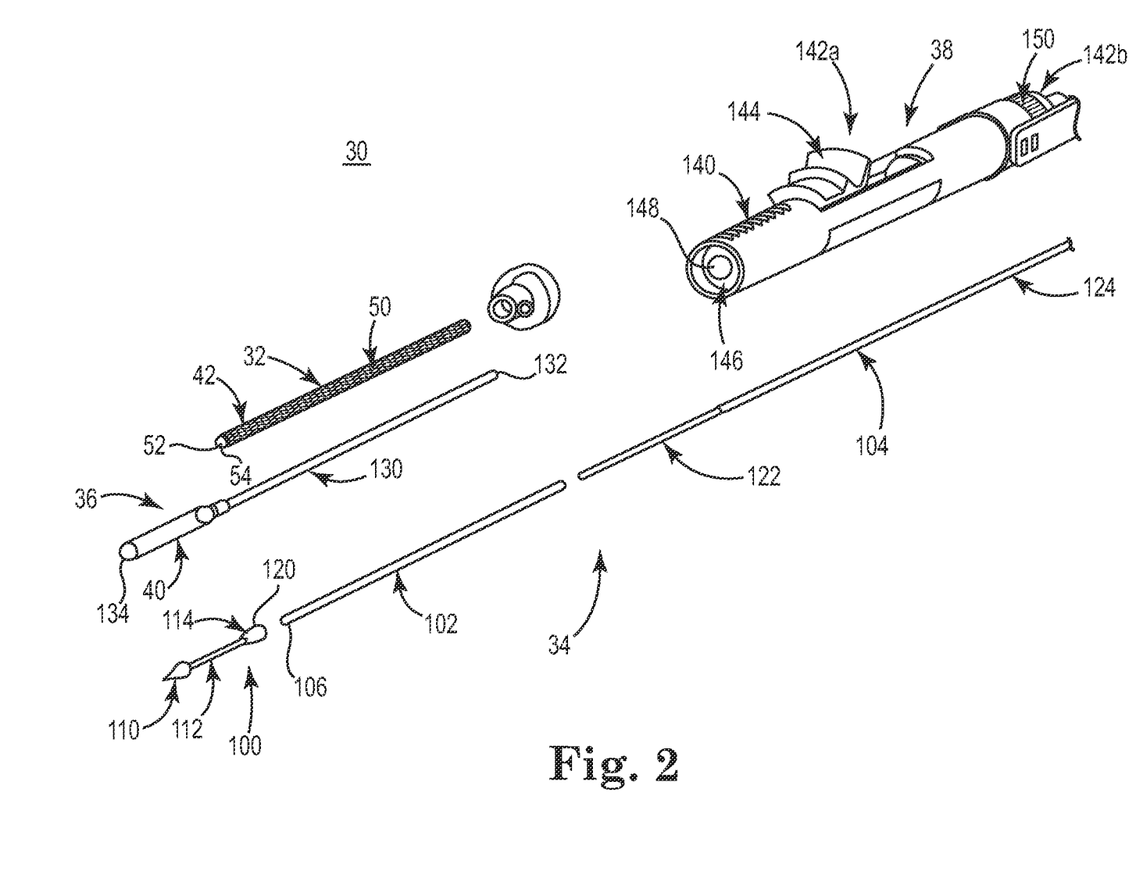
FIG. 2 is an exploded, perspective view of a delivery system in accordance with principles of the present disclosure and useful for percutaneously delivering a stented prosthetic heart valve to a heart valve implantation site.

With the above in mind, one embodiment of a transcatheter stented prosthetic heart valve delivery system 30 is shown in FIG. 2. The system 30 generally includes a recapture assembly 32, an inner shaft assembly 34, a delivery sheath assembly 36, and a handle 38. Details on the various components are provided below. In general terms, however, the delivery system 30 provides a loaded state in which a stented prosthetic heart valve (not shown) is coupled to the inner shaft assembly 34 and compressively retained within a capsule 40 of the delivery sheath assembly 36. The delivery sheath assembly 36 can be manipulated to withdraw the capsule 40 proximally from the prosthetic heart valve via operation of the handle 38, permitting the prosthesis to self-expand and release from the inner shaft assembly 34. Further, the handle 38 can be operated to maneuver the recapture assembly 32 relative to the inner shaft assembly 34 and the delivery sheath assembly 36 to position a recapture frame 42 and corresponding sleeve 50 (referenced generally) of the recapture assembly 32 distally beyond the capsule 40, permitting the recapture assembly 32 to self-expand, and over a partially deployed region of the prosthetic heart valve to facilitate recapturing of the prosthesis within the capsule 40. As a point of reference, various features of the components 32-38 reflected in FIG. 2 and described below can be modified or replaced with differing structures and/or mechanisms. Thus, the present disclosure is in no way limited to the inner shaft assembly 34, the delivery sheath assembly 36, the handle 38, etc., as shown and described below. More generally, delivery systems in accordance with the present disclosure provide features capable of compressively retaining a self-deploying, stented prosthetic heart valve (e.g., the capsule 40), a mechanism capable of effectuating release or deployment of the prosthesis (e.g., retracting the capsule 40), and a structure (e.g., the recapture assembly 32) that promotes recapture.

The recapture assembly 32 includes the recapture frame 42 and the sleeve 50 secured to the frame 42. The recapture assembly 32 also forms a lumen 52 (referenced generally) sized to be slidably received over the inner shaft assembly 34, with the recapture assembly 32 terminating at a distal end 54. With the one construction of FIG. 2, the recapture assembly 32 is provided apart from the delivery sheath assembly 36, and is sized to be slidably received between the inner shaft assembly 34 and the delivery sheath assembly 36. As such, an overall profile of delivery system 30 can be maintained without the need to accommodate a thickness of the recapture assembly 32. Additionally, the recapture assembly 32 can be a variety of different lengths, as compared with a length of the capsule 40, such as half the length of the capsule 40, equal to the length of capsule 40, greater than the length of capsule 40, etc.

Figure 3:
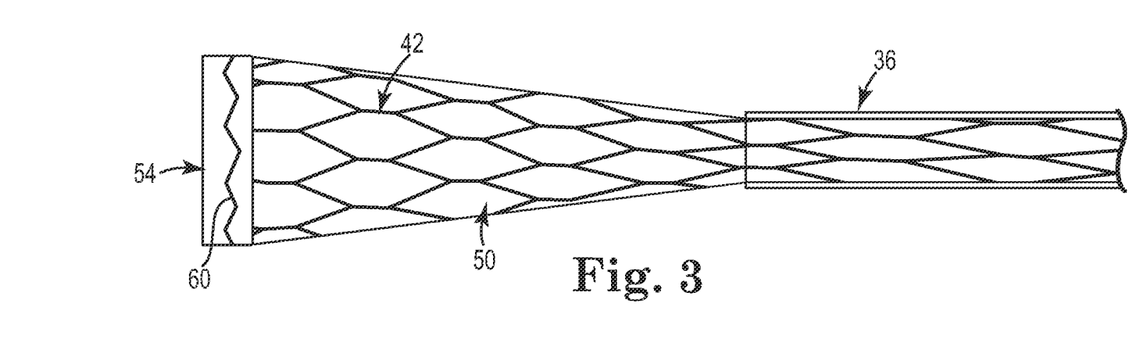
FIG. 3 is a side view of the recapture assembly of FIG. 2 in a partially expanded condition.

The recapture frame 42 is configured to be radially expandable from the compressed arrangement of FIG. 2 having a relatively small, relatively uniform diameter to a radially expanded arrangement. In one embodiment, frame 42 is configured similar to the stent frame discussed above, wherein as forces are released on recapture frame 42 (e.g., as delivery sheath assembly 36 is retracted relative to the recapture assembly 32), a diameter of the distal end 54 is radially increased, as illustrated in FIG. 3. In one embodiment, frame 42 can be configured to create a funnel shape 56 with an increasing distal diameter so as to be configured to recapture a partially deployed prosthetic heart valve. As best shown in FIG. 3, in some embodiments the frame 42 includes a series of wires or wire segments capable of self-transitioning from the collapsed arrangement to the normal, radially expanded arrangement. In turn, the frame 42 creates a columnar strength within the recapture assembly 32. The funnel shape 56 can be formed as a characteristic of the frame 42, sleeve 50, radial strength of the delivery sheath assembly 36 and/or combinations thereof.

In some constructions, a number of individual wires comprising a support structure of the recapture frame 42 can be formed of a metal or other material. These wires are arranged in such a way that the recapture frame support structure allows for folding or compressing or crimping to the compressed arrangement in which the internal diameter is smaller than the internal diameter when in the natural, expanded arrangement. In the collapsed arrangement, such a recapture frame support structure can be mounted onto delivery system 30. The recapture frame support structures are configured so that they can be changed to their natural, expanded arrangement when desired, such as by the relative movement of one or more sheaths relative to a length of the recapture frame 42.

The wires of these recapture frame support structures in embodiments of the present disclosure can be formed from a shape memory material such as a nickel titanium alloy (e.g., Nitinol™). With this material, the support structure is self-expandable from the compressed arrangement to the natural, expanded arrangement, such as by the application of heat, energy, and the like, or by the removal of external forces (e.g., compressive forces). This recapture frame support structure can also be compressed and re-expanded multiple times without damaging the structure of the recapture frame 42. In addition, the recapture frame support structure of such an embodiment may be laser-cut from a single piece of material or may be assembled from a number of different components. In any event, the recapture frame 42 can be embodied in a number of different ways, for example creating the wire structure as illustrated in FIG. 3. The wire structure can include an arrangement of wires and/or struts arranged in various patterns that are configured to expand so as to recapture a prosthetic heart valve that has at least been partially deployed. In other embodiments, the frame 42 can include longitudinally spaced rings that are coupled together through the sleeve 50. The longitudinally spaced rings can be configured to expand to a larger diameter as compressive forces are released on the frame 42. In other embodiments, the rings may include an undulating pattern. In still further embodiments, the rings can be connected by longitudinal struts.

The sleeve 50 is a surgically safe, compliant polymeric material or film positioned on an interior side of the recapture frame 42 and, in the embodiment shown, wrapped around and folded over the frame 42 at distal end 54 of the recapture assembly 32 so as to create a smooth edge to prevent a frame of a prosthetic heart valve from becoming stuck on the recapture frame 42. However, it is not necessary for sleeve 50 to be folded over distal end 54. In other embodiments, sleeve 50 can be bonded, molded, overjacketed, etc. to frame 42. In one example, sleeve 50 is formed of polyethylene terephthalate (PETE), although other materials can also be used. In the embodiment illustrated, sleeve 50 is folded over and attached to frame 42 using a stitch 60, although in other embodiments the sleeve 50 is attached to frame 42 by other means of attachment. With this construction, the sleeve 50 allows the frame 42 to freely deflect or expand, as shown in the expanded condition of FIG. 3. While the sleeve 50 can be elastically deformable, the sleeve 50 can also provide resistance to continued deflection of the frame 42 beyond a certain level of deflection. Thus, in one embodiment the sleeve 50 can control the length and angle of a taper defined by the funnel shape 56 of frame 42 in the expanded arrangement. In any event, sleeve 50 provides a surface to easily engage a prosthetic heart valve.

Returning to FIG. 2, the remaining components 34-38 of the delivery system 30 can assume a variety of forms appropriate for percutaneously delivering and deploying a stented self-expanding prosthetic heart valve. For example, the inner shaft assembly 34 can have various constructions appropriate for supporting a stented prosthetic heart valve within the capsule 40. In some embodiments, the inner shaft assembly 34 can include a retention member 100, an intermediate tube 102, and a proximal tube 104. In general terms, the retention member 100 can be akin to a plunger, and incorporates features for retaining the stented prosthetic heart valve within the capsule 40 as described below. The tube 102 connects the retention member 100 to the proximal tube 104, with the proximal tube 104, in turn, coupling the inner shaft assembly 34 with the handle 38. The components 100-104 can combine to define a continuous lumen 106 (referenced generally) sized to slidably receive an auxiliary component such as a guide wire (not shown).

The retention member 100 can include a tip 110, a support tube 112, and a hub 114. The tip 110 forms or defines a nose cone having a distally tapering outer surface adapted to promote atraumatic contact with bodily tissue. The tip 110 can be fixed or slidable relative to the support tube 112. The support tube 112 extends proximally from the tip 110 and is configured to internally support a compressed, stented prosthetic heart valve generally disposed thereover, and has a length and outer diameter corresponding with dimensional attributes of the selected prosthetic heart valve. The hub 114 is attached to the support tube 112 opposite the tip 110 (e.g., an adhesive bond), and provides a coupling structure 120 (referenced generally) configured to selectively capture a corresponding feature of the prosthetic heart valve. The coupling structure 120 can assume various forms, and is generally located along an intermediate portion of the inner shaft assembly 34. In some constructions, the coupling structure 120 includes one or more fingers sized to be received within corresponding apertures formed by the prosthetic heart valve stent frame (e.g., the prosthetic heart valve stent frame can form wire loops at a proximal end thereof that are received over respective ones of the fingers when compressed within the capsule 40).

The intermediate tube 102 is formed of a flexible polymer material (e.g., PEEK), and is sized to be slidably received within the delivery sheath assembly 36. The proximal tube 104 can include, in some embodiments, a leading portion 122 and a trailing portion 124. The leading portion 122 serves as a transition between the intermediate and proximal tubes 102, 104 and thus in some embodiments is a flexible polymer tubing (e.g., PEEK) having a diameter slightly less than that of the intermediate tube 102. The trailing portion 124 has a more rigid construction, configured for robust assembly with the handle 38 such as a metal hypotube. Other constructions are also envisioned. For example, in other embodiments, the intermediate and proximal tubes 102, 104 are integrally formed as a single, homogenous tube or solid shaft.

The delivery sheath assembly 36 includes the capsule 40 and a delivery sheath shaft 130, and defines proximal and distal ends 132, 134. The capsule 40 extends distally from the delivery shaft 130, and in some embodiments has a more stiffened construction (as compared to a stiffness of the delivery shaft 130) that exhibits sufficient radial or circumferential rigidity to overtly resist the expected expansive forces of the stented prosthetic heart valve in the compressed arrangement. For example, the delivery shaft 130 can be a polymer tube embedded with a metal braiding, whereas the capsule 40 is a laser-cut metal tube. Alternatively, the capsule 40 and the delivery shaft 130 can have a more uniform construction (e.g., a continuous polymer tube). Regardless, the capsule 40 is constructed to compressively retain the stented prosthetic heart valve at a predetermined diameter when loaded within the capsule 40, and the delivery shaft 130 serves to connect the capsule 40 with the handle 38. The delivery shaft 130 (as well as the capsule 40) is constructed to be sufficiently flexible for passage through a patient's vasculature, yet exhibit sufficient longitudinal rigidity to effectuate desired axial movement of the capsule 40. In other words, proximal retraction of the delivery shaft 130 is directly transferred to the capsule 40 and causes a corresponding proximal retraction of the capsule 40. In other embodiments, the delivery shaft 130 is further configured to transmit a rotational force or movement onto the capsule 40.

The handle 38 generally includes a housing 140 and one or more actuator mechanisms 142 (referenced generally). The housing 140 maintains the actuator mechanism(s) 142, with the handle 38 configured to facilitate sliding movement of the delivery sheath assembly 36 relative to the recapture assembly 32 and the inner shaft assembly 34, as well as the recapture assembly 32 relative to the inner shaft assembly 34 and the delivery sheath assembly 36. The housing 140 can have any shape or size appropriate for convenient handling by a user. In one simplified construction, a first, deployment actuator mechanism 142a includes a user interface or actuator 144 slidably retained by the housing 140 and coupled to a delivery sheath connector body 146. The proximal end 132 of the delivery sheath assembly 36 is connected to the delivery sheath connector body 146. The inner shaft assembly 34, and in particular the proximal tube 104, is slidably received within a passage 148 (referenced generally) of the delivery sheath connector body 146, and is rigidly coupled to the housing 140. A second, recapture actuator mechanism 142b (referenced generally) similarly includes a user interface or actuator 150 moveably maintained by the housing 140 and coupled to the recapture assembly 32 via one or more bodies (not shown) facilitating movement of the recapture assembly 32 with operation of the recapture actuator 150. With this but one acceptable construction, the deployment actuator 144 can be operated to effectuate axial movement of the delivery sheath assembly 36 relative to the recapture assembly 32 and the inner shaft assembly 34. Similarly, the recapture actuator 150 can be manipulated to axially slide the recapture assembly 32 relative to the inner shaft assembly 34 and the delivery sheath assembly 36.

Figure 4A:
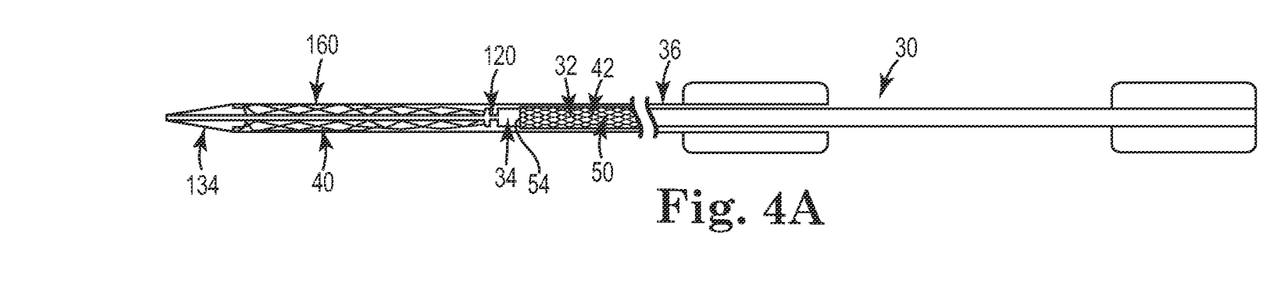
FIGS. 4A-4E are simplified, cross-sectional views illustrating use of the delivery system of FIG. 2 in implanting a stented prosthetic heart valve, including partial deployment and repositioning thereof.

FIG. 4A illustrates, in simplified form, loading of a stented prosthetic heart valve 160 within the delivery system 30. In the loaded state of FIG. 4A, the prosthetic heart valve 160 is crimped over the inner shaft assembly 34, such that the prosthetic heart valve 160 engages the coupling structure 120. The capsule 40 compressively contains the prosthetic heart valve 160 and recapture assembly 32 in the compressed arrangement. Finally, the distal end 54 of the recapture assembly 32 is longitudinally spaced from the prosthetic heart valve 160, with the frame 42 assuming the compressed condition described above. For example, with the arrangement of FIG. 4A, the recapture assembly distal end 54 is proximally spaced from the prosthetic heart valve 160. As implicated by FIG. 4A, then, the capsule 40 exhibits sufficient structural integrity to compressively maintain the prosthetic heart valve 160 in the compressed arrangement without the frame 42, or any other portion of the recapture assembly 32, being disposed over the prosthetic heart valve 160 in the loaded state.

To deploy the prosthetic heart valve 160 from the delivery system 30, the delivery sheath assembly 36 is withdrawn from over the prosthetic heart valve 160, for example by proximally retracting the capsule 40, such that the capsule distal end 134 is proximal the coupling structure 120. Once the capsule 40 is proximal the coupling structure 120, the prosthetic heart valve 160 is allowed to self-expand to a natural arrangement thereby releasing from the delivery system 30.

Figure 4B:
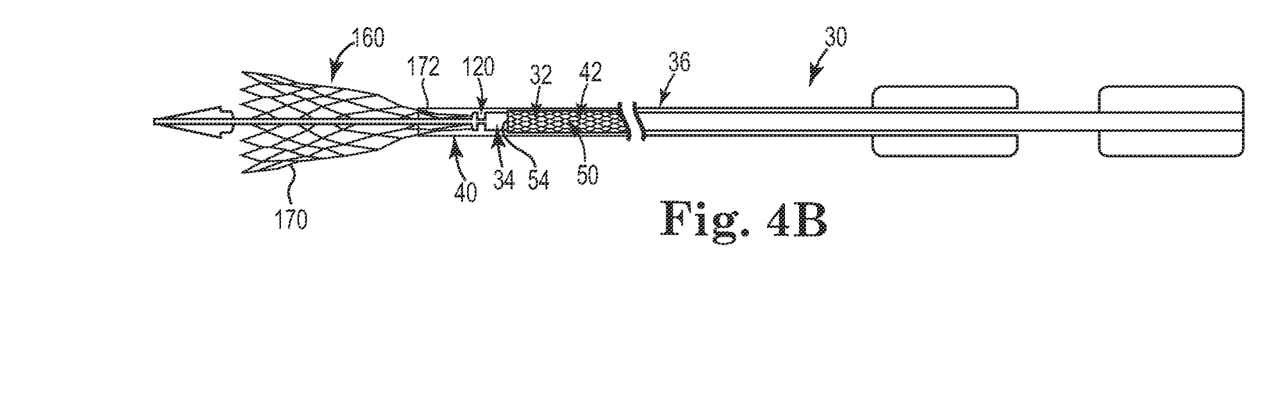

In some instances, a clinician may desire to only partially deploy the prosthetic heart valve 160 and then evaluate before fully releasing the prosthetic heart valve 160. For example, the delivery system 30 loaded with the prosthetic heart valve 160 can be employed as part of a method to repair a damaged heart valve of a patient. Under these circumstances, the delivery system 30, in the loaded state, is advanced toward the native heart valve implantation target site, for example in a retrograde approach, through a cut-down to the femoral artery and into the patient's descending aorta. The delivery system 30 is then advanced, under fluoroscopic guidance, over the aortic arch, through the ascending aorta, and midway across the defective aortic valve (for aortic valve replacement). Once positioning of the delivery system 30 is estimated, the delivery sheath assembly 36, and in particular the capsule 40, is partially retracted relative to the prosthetic heart valve 160 as shown in FIG. 4B. A distal region 170 of the prosthesis 160 is thus exteriorly exposed relative to the capsule 40 and self-expands. In the partially deployed arrangement of FIG. 4B, however, at least a proximal region 172 of the prosthesis 160 remains within the confines of the capsule 40, and thus coupled to the delivery system 30. In this partially deployed state, a position of the stented prosthetic heart valve 160 relative to the desired implantation site can again be evaluated.

Figure 4C:
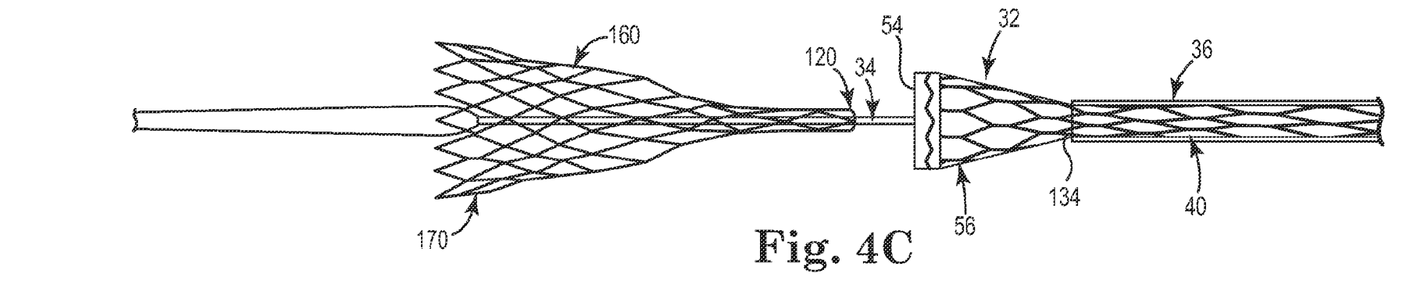

In the event the clinician believes, based upon the above evaluation, that the prosthesis 160 should be repositioned relative to the implantation site, the prosthetic heart valve 160 must first be contracted and "resheathed" by transitioning the delivery system 30 to a recapturing state. As shown in FIG. 4C, the recapture assembly 32 is distally advanced relative to the delivery sheath assembly 36. In particular, the frame 42 and sleeve 50 are distally advanced beyond the distal end 134 of the capsule 40. Due to the distal advancement of the recapture assembly 32, recapture frame 42 expands, forming the funnel shape 56 with a distally increasing diameter. In particular, the frame 42 deflects radially outwardly in response to retraction of the delivery sheath assembly 38 and/or distal advancement of recapture assembly 32. As discussed above, the funnel shape 56 can be formed by frame 42, sleeve 50, capsule 40 and/or combinations thereof. The recapture assembly is maneuvered into contact with the exposed distal region 170 of the prosthetic heart valve 160. The sleeve 50 readily slides along a surface of the prosthetic heart valve 160, with the distal end 54 gently engaging the distal region.

Figure 4D:
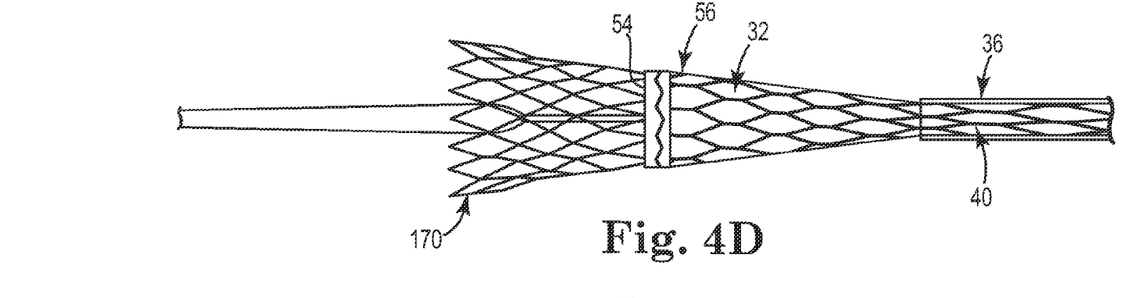
Figure 4E:
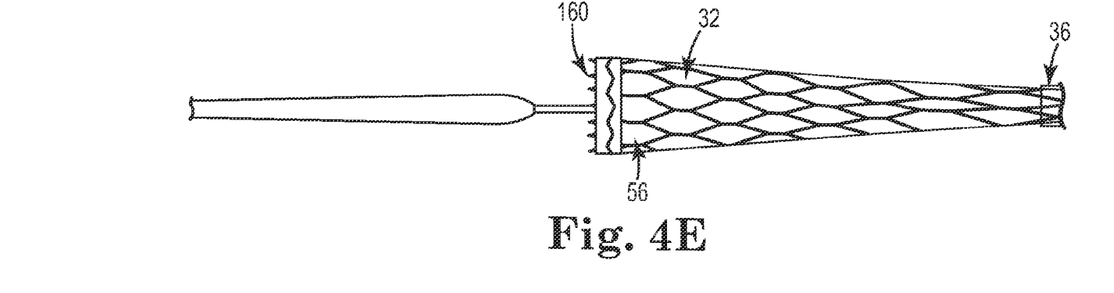

Distal advancement of the recapture assembly 32 continues along the prosthetic heart valve 160 as shown in FIG. 4D. While the distal region 170 may or may not slightly compress in response to placement within the recapture assembly 32, complete compression of the prosthetic heart valve 160 does not occur. However, due to the funnel shape 56, compressive forces required to recapture the prosthetic heart valve 160 are reduced. As shown in FIG. 5E, the recapture assembly 32 is subsequently distally advanced, forming an enclosed region that can be repositioned and/or retracted.

Once the prosthetic heart valve 160 is recaptured, the delivery system 30 can be repositioned relative to the implantation site, and the process repeated until the clinician is comfortable with the achieved positioning. Alternatively, the resheathed stented prosthetic heart valve 160 can be removed from the patient.

The systems and methods of the present disclosure provide a marked improvement over previous designs. By providing an expandable recapture assembly apart from the delivery sheath capsule otherwise utilized to compressively retain the stented prosthetic heart valve, a partially deployed prosthesis is more readily recaptured.

Although the present disclosure has been described with reference to preferred embodiments, workers skilled in the art will recognize that changes can be made in form and detail without departing from the spirit and scope of the present disclosure.

What is claimed is:

1. A delivery system for percutaneously deploying a stented prosthetic heart valve transitionable between a first arrangement defining a first diameter and a second arrangement defining a second diameter greater than the first diameter, the system comprising:
    an inner shaft assembly including an intermediate portion providing a coupling structure configured to selectively engage the stented prosthetic heart valve;
    a delivery sheath capsule slidably disposed over the inner shaft assembly and configured to compressively contain the stented prosthetic heart valve engaged with the coupling structure; and
    a recapture assembly slidably disposed over the inner shaft assembly, the recapture assembly including a recapture frame and a sleeve coupled to the frame, wherein the frame is transitionable from a compressed arrangement to an expanded arrangement in which the frame has a distally increasing diameter;
    wherein the system is configured to provide a loaded state in which the capsule compressively retains the stented prosthetic heart valve over the inner shaft assembly and the recapture assembly is longitudinally displaced from the stented prosthetic heart valve and wherein the system is further configured to provide a recapturing state in which a distal region of the stented prosthetic heart valve is distal the capsule and the recapture assembly is slidably disposed over the stented prosthetic heart valve distal the capsule in order to compress the stented prosthetic heart valve to a third arrangement, wherein a maximum diameter of the stented prosthetic heart valve in the third arrangement is greater than the first diameter and less than the second diameter.

2. The system of claim 1, wherein the delivery sheath capsule is provided as part of a delivery sheath assembly further including a delivery sheath shaft, and further wherein the recapture assembly is slidably disposed between the delivery sheath assembly and the inner shaft assembly.

3. The system of claim 1, wherein the frame is configured to provide columnar strength to the recapture assembly.

4. The system of claim 1, wherein the sleeve is attached to the frame using a stitch.

5. The system of claim 1, wherein the recapture frame includes a wire frame formed of a shape memory material.

6. The system of claim 1, wherein the sleeve is formed of a polymeric material.

7. The system of claim 1, wherein the recapture frame forms a support structure defining an internal surface and wherein the sleeve is attached to the internal surface.

8. The system of claim 1, wherein upon retraction of the delivery sheath capsule relative to the recapture assembly, the recapture frame transitions to the expanded arrangement.

9. A device for repairing a heart valve of a patient, the device comprising:
    a delivery system including:
        an inner shaft assembly including an intermediate portion providing a coupling structure,
        a delivery sheath capsule slidably disposed over the inner shaft assembly,
        a recapture assembly slidably disposed over the inner shaft assembly, the recapture assembly including a recapture frame and a sleeve attached to the recapture frame, wherein the frame is transitionable from a compressed arrangement to an expanded arrangement in which the frame has a distally increasing diameter; and
    a prosthetic heart valve having a stent frame and a valve structure attached to the stent frame and forming at least two valve leaflets, the prosthetic heart valve being self-expandable from a compressed arrangement defining a first diameter to a natural arrangement defining a second diameter greater than the first diameter;
    wherein the device is configured to be transitionable between:
        a loaded state in which the prosthetic heart valve engages the coupling structure and is compressively retained within the capsule portion, the recapture assembly being longitudinally spaced from the prosthetic heart valve in the loaded state,
        a partially deployed state in which the capsule is at least partially withdrawn from the prosthetic heart valve such that a distal region of the prosthetic heart valve is exposed relative to the capsule and self-expands, and
        a recapturing state in which the recapture assembly is distal the capsule and positioned along the distal region of the prosthetic heart valve, causing the recapture frame to expand to the expanded arrangement and the prosthetic heart valve to compress to a recaptured arrangement defining a maximum diameter that is greater than the first diameter and less than the second diameter.

10. The device of claim 9, wherein the delivery sheath capsule is provided as part of a delivery sheath assembly further including a delivery sheath shaft, and further wherein the recapture assembly is slidably disposed between the delivery sheath assembly and the inner shaft assembly.

11. The device of claim 9, wherein the frame is configured to provide columnar strength to the recapture assembly for sliding the recapture assembly over the prosthetic heart valve.

12. The device of claim 9, wherein the recapture frame includes a wire frame formed of a shape memory material.

13. The device of claim 9, wherein the sleeve is formed of a polymeric material.

14. The device of claim 9, wherein the recapture frame forms a support structure defining an internal surface and wherein the sleeve is attached to the internal surface.

15. The device of claim 9, wherein upon retraction of the delivery sheath capsule relative to the recapture assembly, the recapture frame transitions to the expanded arrangement.

* * * * *